US011776121B2

(12) United States Patent
Choi et al.

(10) Patent No.: US 11,776,121 B2
(45) Date of Patent: Oct. 3, 2023

(54) METHOD AND APPARATUS FOR PROVIDING INFORMATION NEEDED FOR DIAGNOSIS OF LYMPH NODE METASTASIS OF THYROID CANCER

(71) Applicant: PHENOMX INC., Seoul (KR)

(72) Inventors: June Young Choi, Seongnam-si (KR); Srinivasan Girish, Palatine, IL (US); Han Suk Kim, Suwon-si (KR); Young Sung Yu, Seoul (KR); Jae Woo Pi, Namyangju-si (KR); Perumalla Akhila, Seongnam-si (KR)

(73) Assignee: PHENOMX INC., Seoul (KR)

( * ) Notice: Subject to any disclaimer, the term of this patent is extended or adjusted under 35 U.S.C. 154(b) by 0 days.

(21) Appl. No.: 17/928,218

(22) PCT Filed: Sep. 29, 2021

(86) PCT No.: PCT/KR2021/013298
§ 371 (c)(1),
(2) Date: Nov. 28, 2022

(87) PCT Pub. No.: WO2013/282388
PCT Pub. Date: Jan. 12, 2023

(65) Prior Publication Data
US 2023/0196561 A1    Jun. 22, 2023

(30) Foreign Application Priority Data
Jul. 9, 2021  (KR) .......................... 10-2021-0090171

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/4227* (2013.01); *A61B 5/4842* (2013.01);
(Continued)

(58) Field of Classification Search
CPC ..................... G06T 7/0012; G06T 7/11; G06T 2207/10081; G06T 2207/20081;
(Continued)

(56) References Cited

U.S. PATENT DOCUMENTS

2019/0259159 A1 *   8/2019   Udupa ................... G16H 30/40

FOREIGN PATENT DOCUMENTS

KR    10-2020-0087427 A    7/2020

OTHER PUBLICATIONS

Kavitha, MuthuSubash et al. "Deep learning enables automated localization of the metastatic lymph node for thyroid cancer on 131I post-ablation whole-body planar scans." Scientific reports vol. 10,1 7738. May 8, 2020, doi:10.1038/s41598-020-64455-w (Year: 2020).*
(Continued)

*Primary Examiner* — Nay A Maung
*Assistant Examiner* — Jose M Torres
(74) *Attorney, Agent, or Firm* — Bridgeway IP Law Group, PLLC; Sang Ho Lee; Hyun Woo Shin (57) ABSTRACT

Provided is a method and apparatus for providing information needed for the diagnosis of lymph node metastasis of a thyroid cancer, and the method includes the steps of: acquiring medical images produced correspondingly to the continuous volumes of a body region including the neck; detecting at least one or more lymph nodes from the medical images through a first network function learned, the lymph nodes including at least one or more lymph nodes having higher lymph node metastasis risks than a given reference value; dividing the neck tissue around the thyroid into a plurality of compartments on the medical images through a
(Continued)

second network function learned, based on the anatomical characteristics of the neck tissue; and matching diagnostic information including the information of the detected lymph nodes and the plurality of compartments with the medical images and displaying the diagnostic information on the medical images.

7 Claims, 8 Drawing Sheets (51) Int. Cl.
    *G06T 7/11*     (2017.01)
    *G06V 20/70*     (2022.01)

(52) U.S. Cl.
    CPC ............... *G06T 7/11* (2017.01); *G06V 20/70* (2022.01); *G06T 2207/10081* (2013.01); *G06T 2207/20081* (2013.01); *G06T 2207/20084* (2013.01); *G06T 2207/30004* (2013.01)

(58) Field of Classification Search
    CPC . G06T 2207/20084; G06T 2207/30004; A61B 5/4227; A61B 5/4842; G06V 20/70
    See application file for complete search history.

(56) References Cited

OTHER PUBLICATIONS

Gul et al., "Diagnostic Utility of Radiomics in Thyroid and Head and Neck Cancers", frontiers in Oncology, Jul. 7, 2021, pp. 1-14 (Year: 2021).*
Lee, Jeong Hoon et al., "Application of deep learning to the diagnosis of cervical lymph node metastasis from thyroid cancer with CT". European Radiology (2019) 29:5452-5457.
Xuming Chen et al., "A deep learning-based auto-segmentation system for organs-at-risk on whole-body computed tomography images for radiation therapy". Radiotherapy and Oncology 160 (2021) 175-184.

* cited by examiner

METHOD AND APPARATUS FOR PROVIDING INFORMATION NEEDED FOR DIAGNOSIS OF LYMPH NODE METASTASIS OF THYROID CANCER

TECHNICAL FIELD

The present disclosure relates to a method and apparatus for providing information needed for the diagnosis of lymph node metastasis of a thyroid cancer.

BACKGROUND ART

A computed tomography (CT) scan is used to obtain cross-sectional images of a patient's body, unlike x-ray imaging. The CT scan provides images having a smaller number of structures overlapped than the x-ray imaging, thereby making it possible to more obviously see the structures and lesions on the images. Further, the CT scan is typically less expensive than a magnetic resonance imaging (MRI) scan and has an examination time shorter than the MRI scan, and accordingly, if suspicious lesions appear on organs and diseases to thus need detailed examination, the CT scan is basically performed.

As multi-detector CT (MDCT) scans have prevailed, recently, images are re-constructed after imaging to freely obtain desired cross-sectional images and three-dimensional images, like MRI scans, and further, the CT images are collected in medical organizations.

Further, the CT images are used to check whether a cancer occurs and the cancer causes metastasis, and in conventional practices, a method for checking the cancer or metastasis with a doctor's naked eye is the best. However, the determination of the occurrence of the cancer or metastasis on the medical images requires a high skill level, and if an inspector's fatigue is high, the probability of a misdiagnosis is increased.

To solve such a problem, recently, a medical image analysis technology using artificial intelligence has been developed. According to the medical image analysis technology using artificial intelligence, lesion regions such as cancer metastasis regions are detected using artificial intelligence, without having any reading with the doctor's naked eye. However, the technology just extracts the lesion regions automatically to provide the positions and sizes of the lesions, which causes limitations in determining excising regions upon real surgery.

In the case of both of the reading with the naked eye and the automatic extraction using the artificial intelligence, a biopsy for the tissue around cancer metastasis regions has to be necessarily performed, if the cancer metastasis regions are recognized, to prevent a cancer from returning, and further, the tissue around the cancer metastasis regions has to be excised. In the excising process, if the excised region is too small, the surgery time and cost and hospital admission period may be reduced to help a patient recover within a short time, but the probability of a bad prognosis such as a cancer recurrence may become increased. Contrarily, if the excised region is too large, cost and physical energy loads applied to the patient may be increased.

At a step of building a plan before surgery, accordingly, it is necessary to obtain appropriate excising region and size, but the conventional artificial intelligence-based medical image analysis technologies fail to provide sufficient information needed for building the plan before surgery.

DISCLOSURE

Technical Problem

Accordingly, the present invention has been made in view of the above-mentioned problems occurring in the related art, and it is an object of the present invention to provide a method and apparatus for providing information needed for the diagnosis of lymph node metastasis of a thyroid cancer that is capable of automatically extracting the lymph nodes having cancer metastasis risks from head and neck CT images through deep learning models, matching the extracted information with the neck tissue around the thyroid that is divided into a plurality of compartments, and displaying the information on the CT images more intuitively, thereby enabling the diagnosis and surgical planning for the lymph node metastasis of the thyroid cancer.

The technical problems to be achieved through the present invention are not limited as mentioned above, and other technical problems not mentioned herein will be obviously understood by one of ordinary skill in the art through the following description.

Technical Solution

To accomplish the above-mentioned objects, according to an aspect of the present invention, there is provided a method for providing information needed for the diagnosis of lymph node metastasis of a thyroid cancer, the method including the steps of: acquiring medical images produced correspondingly to the continuous volumes of a body region including the neck; detecting at least one or more lymph nodes from the medical images through a first network function learned, the lymph nodes including at least one or more lymph nodes having higher lymph node metastasis risks than a given reference value; dividing the neck tissue around the thyroid into a plurality of compartments on the medical images through a second network function learned, based on the anatomical characteristics of the neck tissue; and matching diagnostic information including the information of the detected lymph nodes and the plurality of compartments with the medical images and displaying the diagnostic information on the medical images.

According to an exemplary embodiment of the present invention, the diagnostic information may include at least one of the identifiers of the lymph nodes, the position coordinates of the lymph nodes, the volumes of the lymph nodes, the compartments where the lymph nodes are included, and the cancer metastasis risks of the lymph nodes.

According to an exemplary embodiment of the present invention, the method may further include the step of calculating cancer metastasis seriousness, based on at least one of the number of lymph nodes included in the respective compartments, the volumes of the lymph nodes, and the cancer metastasis risks of the lymph nodes, the cancer metastasis seriousness for the respective compartments being included in the diagnostic information.

According to an exemplary embodiment of the present invention, the method may further include the step of setting an excising region among the plurality of compartments, based on the calculated cancer metastasis seriousness.

According to an exemplary embodiment of the present invention, the method may further include the step of calculating the respective volumes of the lymph nodes and the compartments where the lymph nodes are included among the plurality of compartments.

According to an exemplary embodiment of the present invention, the method may further include the step of detecting the thyroid from the medical images through a learned third network function, and the diagnostic information may further include information of the detected thyroid.

According to an exemplary embodiment of the present invention, the method may further include the step of estimating a cancer metastasis process from the detected lymph nodes.

To accomplish the above-mentioned objects, according to another aspect of the present invention, there is provided an apparatus for providing information needed for the diagnosis of lymph node metastasis of a thyroid cancer, the apparatus including: a processor; and a memory for storing a program executable by the processor, wherein the processor executes the program to acquire medical images produced correspondingly to the continuous volumes of a body region including the neck, detect at least one or more lymph nodes from the medical images through a first network function learned, divide the neck tissue around the thyroid into a plurality of compartments on the medical images through a second network function learned, based on the anatomical characteristics of the neck tissue, match diagnostic information including the information of the detected lymph nodes and the plurality of compartments with the medical images, and display the diagnostic information on the medical images, and the lymph nodes include at least one or more lymph nodes having higher lymph node metastasis risks than a given reference value.

Advantageous Effects

According to the embodiments of the present invention, the method and apparatus for providing information needed for the diagnosis of lymph node metastasis of a thyroid cancer can accurately detect the thyroid and the lymph nodes having cancer metastasis risks from the head and neck medical images using the neural network and matching the detected information with the medical images, thereby more intuitively providing the detected information.

According to the embodiments of the present invention, further, the method and apparatus for providing information needed for the diagnosis of lymph node metastasis of a thyroid cancer can divide the neck tissue around the thyroid into the plurality of compartments and provide the information of the lymph nodes included in the respective compartments through the medical images, thereby making it possible for the diagnostician to easily recognize the cancer metastasis seriousness and reducing unnecessary biopsies and over excising.

The effectiveness of the invention is not limited as mentioned above, and it should be understood to those skilled in the art that the effectiveness of the invention may include another effectiveness as not mentioned above from the detailed description of the present invention.

BRIEF DESCRIPTION OF DRAWINGS

Now, a brief description of the drawings is given to allow the drawings suggested in the present invention to be more clearly understood.

MODE FOR INVENTION

The present invention may be modified in various ways and may have several exemplary embodiments. Specific exemplary embodiments of the present invention are illustrated in the drawings and described in detail in the detailed description. However, this does not limit the invention within specific embodiments and it should be understood that the invention covers all the modifications, equivalents, and replacements within the idea and technical scope of the invention.

In the description, if it is determined that the detailed explanation on the well known technology related to the present invention makes the scope of the present invention not clear, the explanation will be avoided for the brevity of the description. Terms, such as the first, the second, and the like may be used to describe various elements, but the elements should not be restricted by the terms. The terms are used to only distinguish one element from the other element.

When it is said that one element is described as being "connected" or "coupled" to the other element, one element may be directly connected or coupled to the other element, but it should be understood that another element may be present between the two elements.

The terms "unit", "-or/er" and "module" described in the specification indicate a unit for processing at least one function or operation, which may be implemented by hardware, software or a combination thereof, such as a processor, a micro processor, a micro controller, a central processing unit (CPU), a graphics processing unit (GPU), an accelerate processor unit (APU), a digital signal processor (DSP), an application specific integrated circuit (ASIC), a field programmable gate array (FPGA), and the like.

Further, it should be appreciated that the division of the parts in the present disclosure is just made according to principal functions the parts have. That is, two or more parts as will be discussed below may be combined to one part or one part may be divided into two or more parts according to more specified functions. Moreover, the respective parts as will be discussed in the specification can additionally perform some or all of functions performed by other parts as well as their main functions, and of course, also, some of the main functions of the respective parts can be performed only by other parts.

Hereinafter, exemplary embodiments of the present invention will be described in detail.

In the description, a network function may be used with the same meaning as a neural network. In this case, the neural network is composed of interconnected calculation units, which are commonly called nodes, and the nodes are called neurons. Generally, the neural network is made up of a plurality of nodes. The nodes for constituting the neural network are connected to one another by means of one or more links.

Some of nodes constituting the neural network build one layer based on their distances from an initial input node. For example, a collection of nodes with the distances of n from the initial input node builds an n layer.

In the description, the neural network may include a deep neural network (DNN) having a plurality of hidden layers as well as input and output layers.

Figure 1:
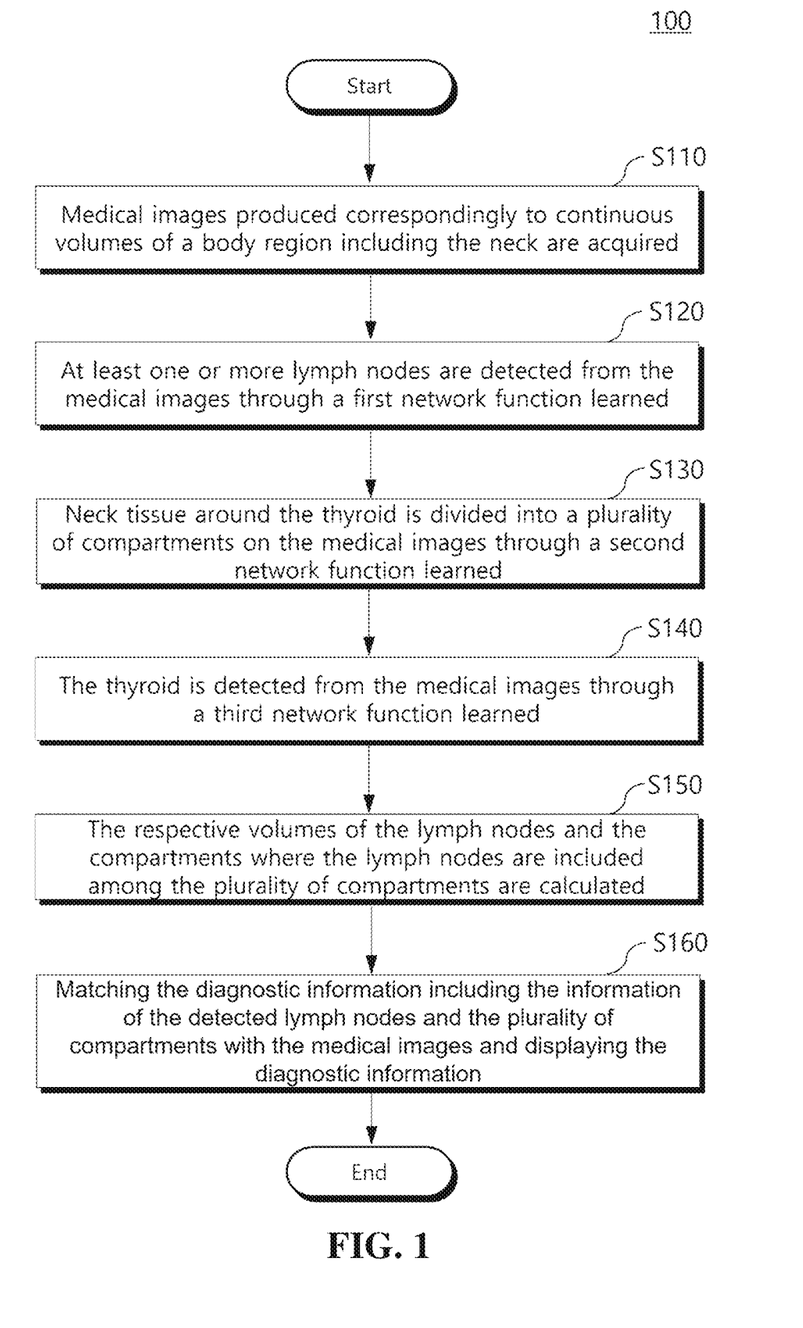
FIG. 1 is a flowchart showing a method for providing information needed for the diagnosis of lymph node metastasis of a thyroid cancer according to an embodiment of the present invention.

FIG. 1 is a flowchart showing a method for providing information needed for the diagnosis of lymph node metastasis of a thyroid cancer according to an embodiment of the present invention.

A method 100 according to the embodiment of the present invention is performed through a personal computer, a work station, a server computer, and the like, which have operation ability, or through a separate device therefor.

Further, the method 100 is performed through one or more operation devices. For example, at least one or more steps of the method 100 according to the embodiment of the present invention are performed through a client device, and other steps through a server device. In this case, the client device and the server device are connected by a network and transmit and receive the results of operations to and from each other. Otherwise, the method 100 according to the present invention is performed through distributed computing.

At step S110, medical images produced correspondingly to continuous volumes of a body region including the neck are acquired. According to the present invention, the medical images are CT images produced through a patient's head and neck CT. That is, the medical images are composed of a plurality of slices produced by continuously imaging the patient's head and neck in one direction through the CT. According to the present invention, further, the medical images are three-dimensional images for the head and neck produced by laminating a plurality of slices constituting the CT images on top of each other.

At step S120, the medical images are inputted to a first network function learned (that is, a lymph node detection module) to detect at least one or more lymph nodes therefrom. According to the present invention, the lymph nodes detected at the step S120 include at least one or more lymph nodes having higher lymph node metastasis risks than a given reference value. For example, the first network function detects at least one or more lymph nodes being suspected of having cancer metastasis and the probability of the cancer metastasis, based on the anatomical characteristics of the lymph nodes having the caner metastasis. Next, the first network function finally detects at least one or more lymph nodes having higher lymph node metastasis risks than the given reference value, based on the corresponding probability.

The first network function has pre-learning for the detection of the lymph nodes through learning data (for example, CT images of the head and neck including the lymph nodes labeled as having cancer metastasis by specialists or inspection).

The information of the detected lymph nodes includes position coordinates of the detected lymph nodes. In this case, the position coordinates of the lymph nodes are produced correspondingly to the same reference coordinates as the medical images produced or converted into the three-dimensional images.

According to embodiments of the present invention, even though not shown, the method 100 further includes the step of labeling the detected lymph nodes. For example, the information of the at least one or more lymph nodes detected by the first network function is displayed with a given method (specific colors, shadow, boundary lines, etc.) on the medical images and provided for a diagnostician, and unique identifiers ID are labeled, by the diagnostician, to the respective lymph nodes, while using the medical images on which the lymph nodes are displayed.

At step S130, the medical images are inputted to a second network function learned (that is, a neck tissue division module) to divide the neck tissue around the thyroid into a plurality of compartments. That is, the second network function detects the neck tissue around the thyroid and divides the neck tissue into the plurality of compartments, based on the anatomical characteristics as the reference of the division. For example, the second network function divides the neck tissue around the thyroid into six to seven compartments, based on the anatomical characteristics such as big blood vessels (such as common carotid artery, internal jugular vein, sternocleidomastoid, and hyoid bone) connected from the heart to the brain.

The second network function has pre-learning for the division of the neck tissue through learning data (for example, CT images of the head and neck on which neck tissue division is performed by specialists).

At step S140, the medical images are inputted to a third network function learned (that is, a thyroid detection module) to detect the thyroid therefrom.

The third network function has pre-learning for the detection of the thyroid through learning data (for example, CT images of the head and neck including the thyroid labeled by specialists).

The information of the thyroid detected at the step S140 is displayed with a given method (specific colors, shadow, boundary lines, etc.) on the medical images and provided for the diagnostician, and based on the information, the shape (swelling, biasing, etc.) of the thyroid is determined by the diagnostician.

Meanwhile, the steps S120 to S140 of FIG. 1 are performed sequentially, but according to the present invention, at least some of the steps S120 to S140 are simultaneously performed or changed in order. For example, the step S140 is first performed, and next, the steps S120 and S130 are performed. That is, the steps S120 to S140 may be performed in a state of being freely changed in order. According to the present invention, otherwise, the step S140 may be omitted.

At steps S150, the respective volumes of the detected lymph nodes and the compartments where the detected lymph nodes are included among the plurality of compartments are calculated. For example, the volumes of the detected lymph nodes in three-dimensional space are calculated through a given calculation expression (for example, the number of voxels that corresponds to X lymph nodes as unit volume of voxel), and the compartments where the respective lymph nodes are included are calculated based on the position coordinates of the lymph nodes.

At step S160, the diagnostic information including the information of the detected lymph nodes, the plurality of compartments, and/or the thyroid matches the medical images and is displayed on the medical images. In this case, the diagnostic information includes the information of the identifiers of the lymph nodes, the position coordinates of the lymph nodes, the volumes of the lymph nodes, the compartments where the lymph nodes are included, the cancer metastasis risks of the lymph nodes, the position of the thyroid, the shape of the thyroid, and/or the compartments of the neck tissue around the thyroid and the positions of the compartments, and the like. For example, the information of the lymph nodes, the plurality of compartments and/or the thyroid is displayed with a given method (specific colors, shadow, boundary lines, etc.) on the three-dimensional medical images, and further, the diagnostic information including the displayed information is displayed in the form of texts and provided for the diagnostician.

According to the embodiment of the present invention, the method 100 further includes the step of estimating a cancer metastasis process for the detected lymph nodes. For example, the metastasis process (or metastasis order) among the plurality of lymph nodes being currently suspected of having cancer metastasis and the probability of the cancer metastasis in the future is estimated, based on the positions of the plurality of lymph nodes, the compartments where the lymph nodes are included, and the volumes of the lymph nodes, and the estimated result is provided for the diagnostician.

According to the embodiment of the present invention, the estimation of the metastasis process among the lymph nodes is performed by a fourth network function learned. For example, the fourth network function has pre-learning for the estimation of the cancer metastasis process among the lymph nodes from the information of the cancer metastasis lymph nodes, such as the positions of the lymph nodes where cancer metastasis occurs, the volumes of the lymph nodes, and the compartments where the lymph nodes are included, and the like, as learning data.

Figure 2:
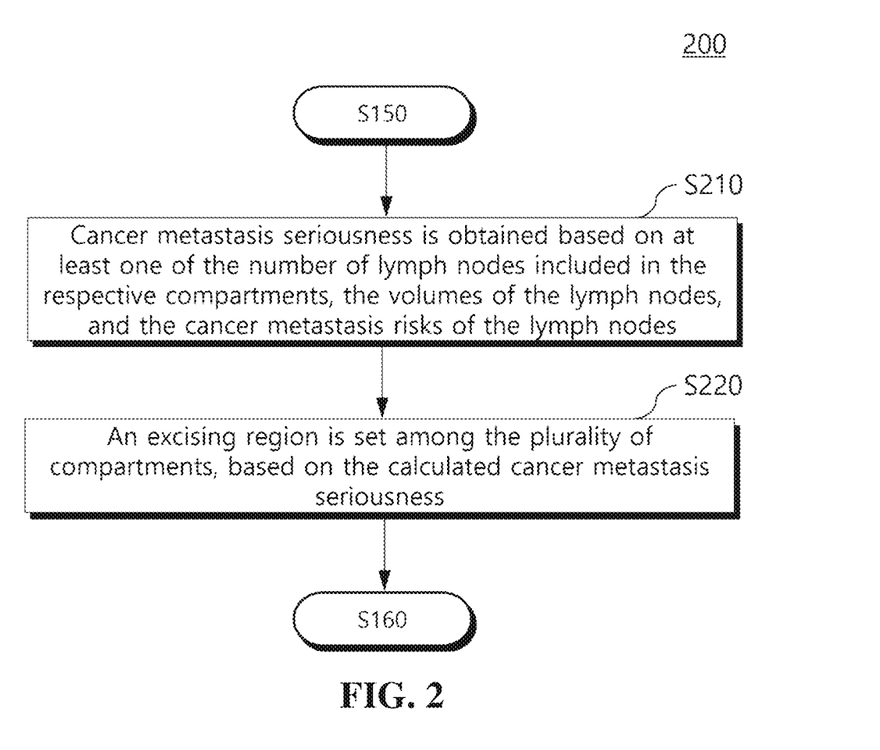
FIG. 2 is a flowchart showing specific steps of the method for providing information needed for the diagnosis of lymph node metastasis of a thyroid cancer according to the embodiment of the present invention.

FIG. 2 is a flowchart showing specific steps of the method for providing information needed for the diagnosis of lymph node metastasis of a thyroid cancer according to the embodiment of the present invention.

As shown in FIG. 2, a method 200 is added to the method 100 of FIG. 1 and includes steps S210 and S220.

At the step S210, cancer metastasis seriousness is obtained based on at least one of the number of lymph nodes included in the respective compartments, the volumes of the lymph nodes, and the cancer metastasis risks of the lymph nodes.

For example, if a number of lymph nodes having cancer metastasis risks exist in a given compartment or the lymph nodes have large volumes and high cancer metastasis risks, the corresponding compartment is calculated as having a high degree of cancer metastasis seriousness.

At the step S220, next, an excising region is set among the plurality of compartments, based on the calculated cancer metastasis seriousness. For example, at least a portion of the compartment having a higher degree of cancer metastasis seriousness than a given reference value is set as the excising region.

The information of the calculated cancer metastasis seriousness of the respective compartments at the step S210 and the set excising region at the step S220 is included in the diagnostic information, displayed on the medical images, and provided for the diagnostician at the step S160.

FIGS. 3 to 6 show a plurality of modules serving as network functions and their exemplary operations so as to perform the method for providing information needed for the diagnosis of lymph node metastasis of a thyroid cancer according to the embodiment of the present invention.

Figure 3:
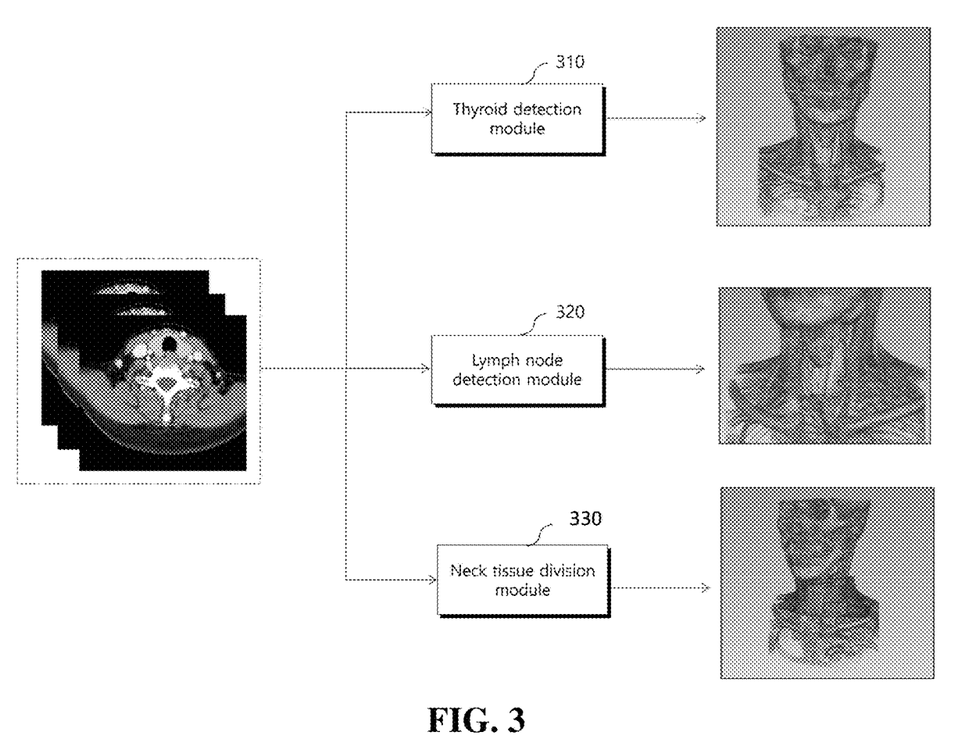
FIGS. 3 to 6 show a plurality of modules serving as network functions and their exemplary operations so as to perform the method for providing information needed for the diagnosis of lymph node metastasis of a thyroid cancer according to the embodiment of the present invention.

Referring to FIG. 3, the medical images produced by imaging the patient's head and neck are inputted to the thyroid detection module 310, the lymph node detection module 320, and the neck tissue division module 330.

In this case, the medical images 10 are the head and neck CT images composed of a group of images having a plurality of two-dimensional slices or the three-dimensional head and neck images produced based on the head and neck CT images. Further, the thyroid detection module 310, the lymph node detection module 320, and the neck tissue division module 330 include the network functions capable of making machine learning or deep learning performed. According to embodiments of the present invention, the respective network functions are capable of making three-dimensional deep learning performed.

Figure 4:
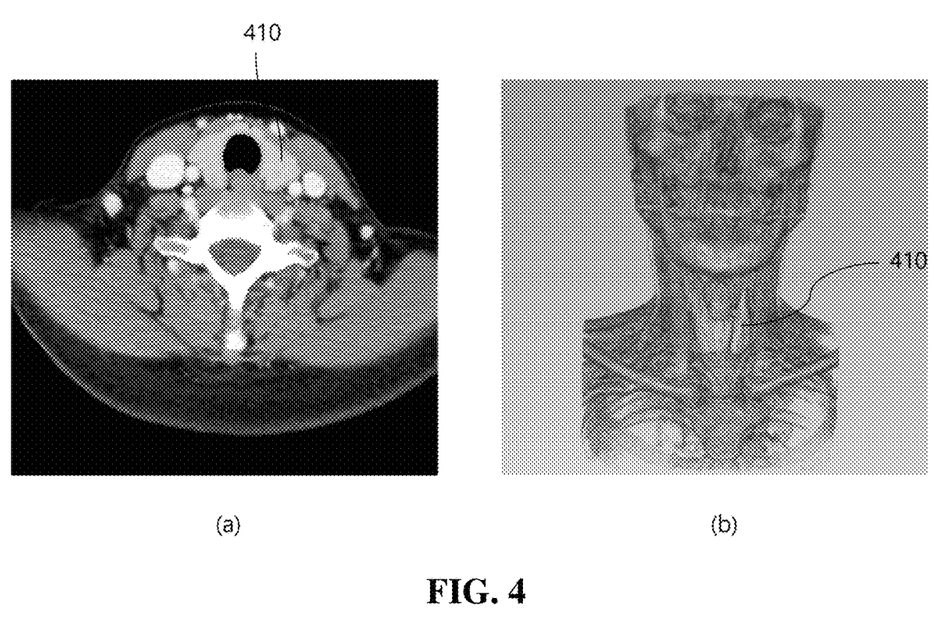

The thyroid detection module 310 detects the thyroid 410 from the medical images inputted thereto, matches the detected information with the medical images, and displays the detected information on the medical images. For example, as shown in FIG. 4, the thyroid detection module 310 displays the region corresponding to the thyroid 410 on the medical images with given shadow, based on the information of the thyroid 410 detected. The display is performed on some of the two-dimensional slides or on the three-dimensional medical images.

Figure 5:
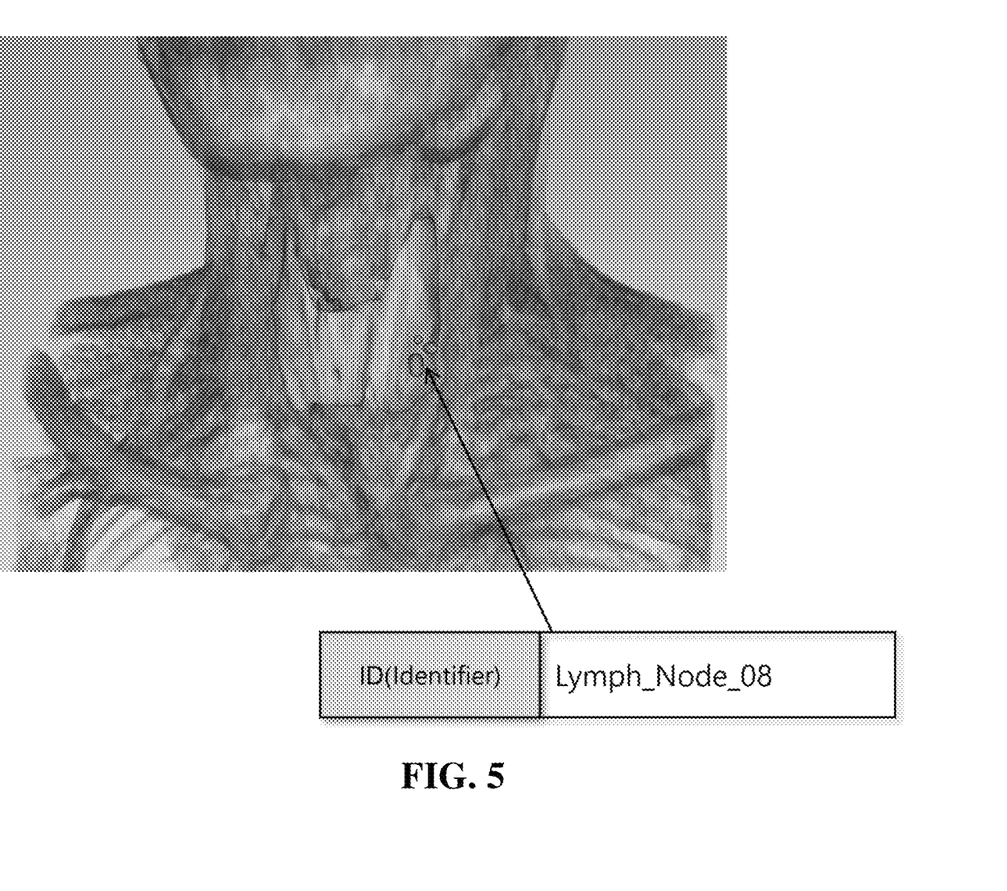

The lymph node detection module 320 detects at least one or more lymph nodes having cancer metastasis risks from the medical images inputted thereto, and as shown in FIG. 5, the lymph node detection module 320 matches the detected information with the medical images and displays it on the medical images. The information of the detected lymph nodes includes the position coordinates of the lymph nodes, the volumes of the lymph nodes and/or the cancer metastasis risks of the lymph nodes.

According to the embodiment of the present invention, further, the lymph node detection module 320 applies unique identifier labels to the detected lymph nodes, based on the user's input.

Figure 6:
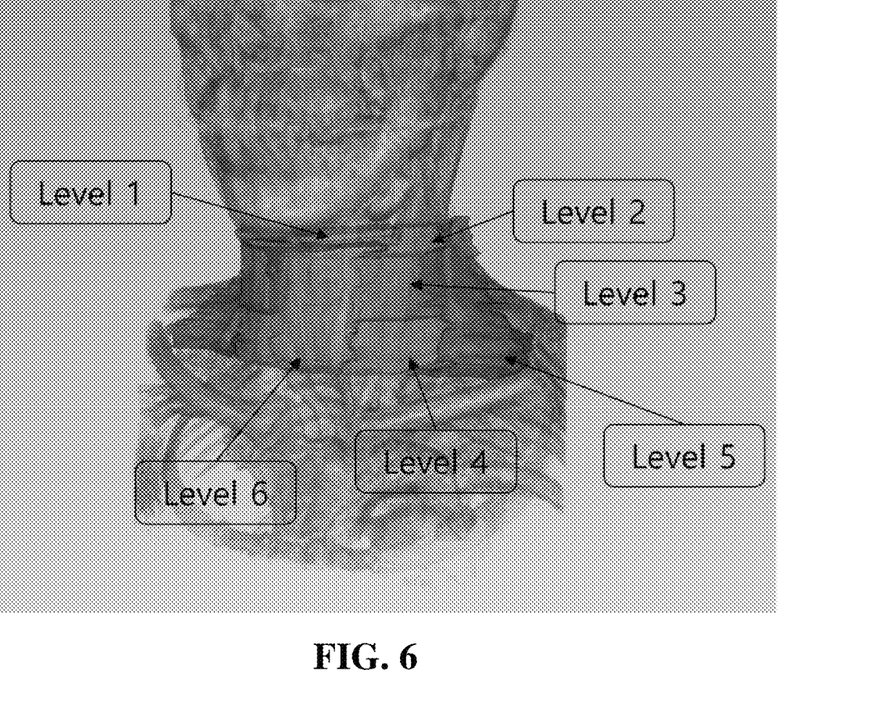

The neck tissue division module 330 detects the neck tissue around the thyroid from the inputted medical images and divides the detected neck tissue into the plurality of compartments, based on the anatomical characteristics of the neck tissue. Further, as shown in FIG. 6, the neck tissue division module 330 matches the information of the plurality of compartments with the medical images and displays it on the medical images. The plurality of compartments are displayed on the medical images, while having different shadow colors.

For example, the plurality of compartments include six compartments divided according to the anatomical characteristics of the neck tissue, and the respective compartments are called levels 1 to 6.

Figure 7:
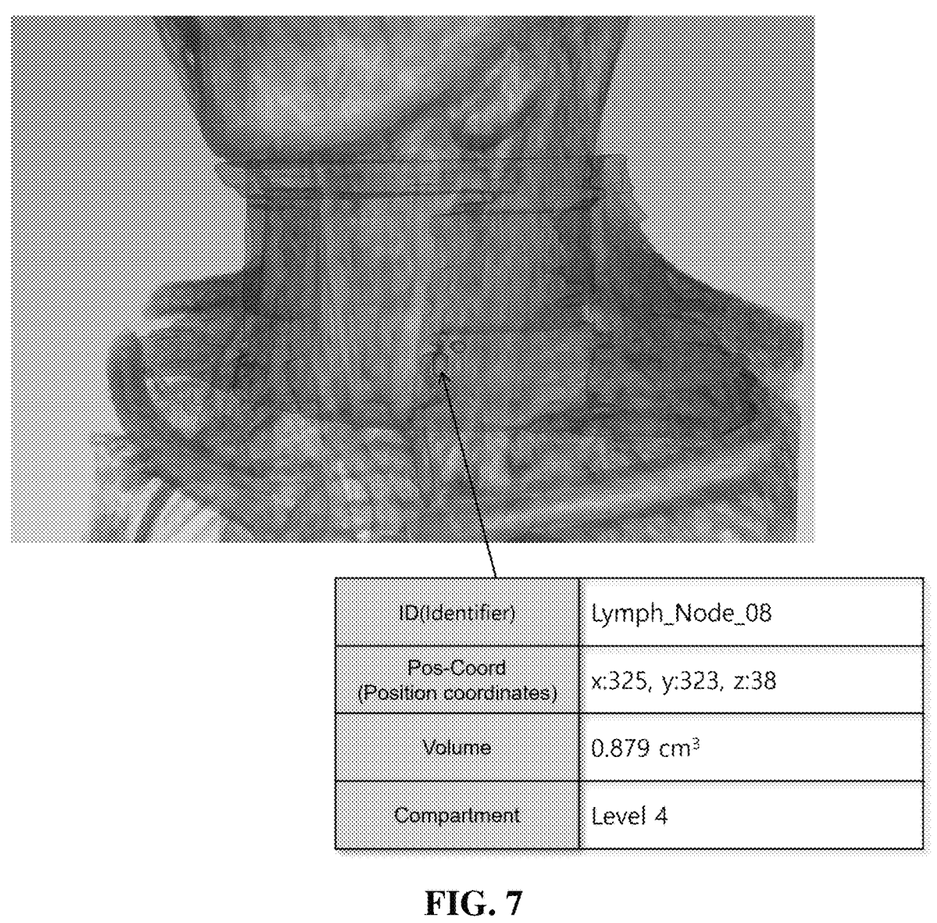
FIG. 7 is an exemplary view showing the diagnostic information provided by using the method for providing information needed for the diagnosis of lymph node metastasis of a thyroid cancer according to the embodiment of the present invention.

FIG. 7 is an exemplary view showing the diagnostic information provided by using the method for providing information needed for the diagnosis of lymph node metastasis of a thyroid cancer according to the embodiment of the present invention.

Referring to FIG. 7, at least some of the information of the thyroid, the lymph nodes and/or the plurality of compartments detected by the thyroid detection module 310, the lymph node detection module 320, and the neck tissue division module 330 are included in the diagnostic information and displayed on the medical images.

For example, the plurality of compartments for the neck tissue match the medical images and are then displayed on the medical images, and the detected lymph nodes are displayed on the medical images, while having given colors. Further, the information of the identifiers, position coordinates, volumes, compartments, and cancer metastasis risks of the respective lymph nodes displayed on the medical images are displayed on the medical images.

Figure 8:
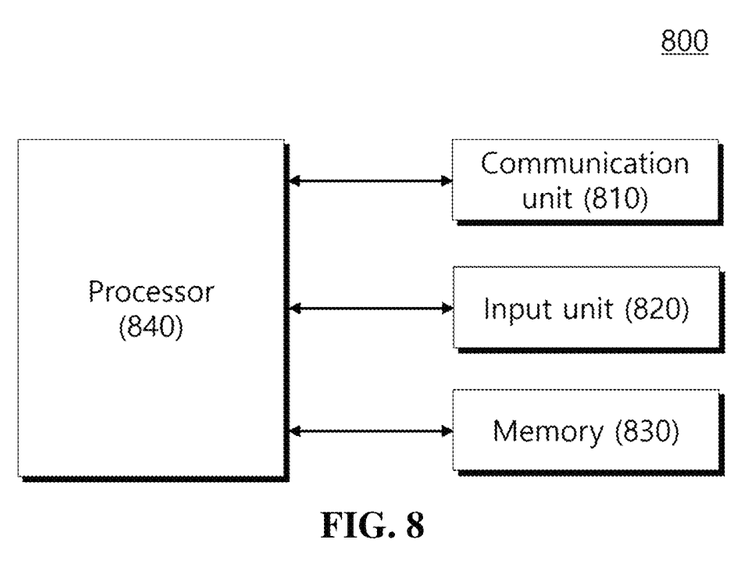
FIG. 8 is a schematic block diagram showing an apparatus for providing information needed for the diagnosis of lymph node metastasis of a thyroid cancer according to the embodiment of the present invention.

FIG. 8 is a schematic block diagram showing an apparatus for providing information needed for the diagnosis of lymph node metastasis of a thyroid cancer according to the embodiment of the present invention.

A communication unit 810 receives input data (head and neck CT images, etc.) for diagnosing whether lymph node metastasis occurs. The communication unit 810 includes wired and wireless communication units. If the communication unit 810 includes the wired communication unit, the communication unit 810 includes one or more components for performing communication with a local area network (LAN), a wide area network (WAN), a value added network (VAN), a mobile radio communication network, a satellite communication network, and a combination thereof. Contrarily, if the communication unit 810 includes the wireless communication unit, the communication unit 810 transmits and receives data or signals wirelessly by using cellular communication, wireless LAN (e.g., Wi-Fi), and the like. According to the present invention, the communication unit 810 transmits and receives data or signals to and from an external device or external server under the control of a processor 840 as will be discussed later.

An input unit 820 receives various user commands through external control. To do this, the input unit 820 includes one or more input devices or is connected to the input devices. For example, the input unit 820 is connected to an interface for various inputs such as a keypad, a mouse, and the like and receives the user commands from the interface. To do this, the input unit 820 includes an interface such as a USB port, a Thunderbolt interface, and the like. Further, the input unit 820 includes various input devices such as a touch screen, a button, and the like or is connected to the input devices to receive the user commands from the outside.

A memory 830 stores programs and/or program commands for operating the processor 840 and temporarily or permanently stores data inputted and outputted. The memory 830 includes at least one storage medium of a flash memory, a hard disc, a multimedia card micro storage medium, a card type memory (e.g., SD or XD memory), random access memory (RAM), a static RAM (SRAM), a read-only memory (ROM), an electrically erasable programmable ROM (EEPROM), a programmable ROM (PROM), a magnetic memory, a magnetic disc, and an optical disc.

Further, the memory 830 stores various network functions and algorithms, while storing various data, programs (with one or more instructions), applications, software, commands, and codes for operating and controlling the apparatus 800 according to the present invention.

The processor 840 controls all of operations of the apparatus 800 according to the present invention. The processor 840 executes one or more programs stored in the memory 830. The processor 840 represents a central processing unit (CPU), a graphics processing unit (GPU), or a dedicated processor through which the method according to the technical ideas of the present invention is performed.

According to the embodiment of the present invention, the processor 840 acquires the medical images produced correspondingly to the continuous volumes of the body region including the neck, detects at least one or more lymph nodes from the medical images through the first network function learned, divides the neck tissue around the thyroid into the plurality of compartments on the medical images through the second network function learned, based on the anatomical characteristics of the neck tissue, and matching diagnostic information including the information of the detected lymph nodes and the plurality of compartments with the medical images and displaying the diagnostic information on the medical images. In this case, the lymph nodes include at least one or more lymph nodes having higher lymph node metastasis risks than the given reference value.

According to the embodiment of the present invention, the processor 840 calculates the cancer metastasis seriousness, based on at least one of the number of lymph nodes included in the respective compartments, the volumes of the lymph nodes, and the cancer metastasis risks of the lymph nodes.

According to the embodiment of the present invention, the processor 840 sets the excising region among the plurality of compartments, based on the calculated cancer metastasis seriousness.

According to the embodiment of the present invention, the processor 840 calculates the respective volumes of the lymph nodes and the compartments where the lymph nodes are included among the plurality of compartments.

According to the embodiment of the present invention, the processor 840 detects the thyroid from the medical images through the third network function learned.

According to the embodiment of the present invention, the processor 840 estimates a cancer metastasis process from the detected lymph nodes.

The various embodiments of the present disclosure as described above may be implemented in the form of a program instruction that can be performed through various computers, and may be recorded in a computer readable recording medium. The computer readable medium may include a program command, a data file, a data structure, and the like independently or in combination. The program instruction recorded in the recording medium is specially designed and constructed for the present disclosure, but may be well known to and may be used by those skilled in the art of computer software. The computer readable recording medium may include a magnetic medium such as a hard disc, a floppy disc, and a magnetic tape, an optical recording medium such as a compact disc read only memory (CD-ROM) and a digital versatile disc (DVD), a magneto-optical medium such as a floptical disk, and a hardware device specifically configured to store and execute program instructions, such as a read only memory (ROM), a random access memory (RAM), and a flash memory. Further, the program command may include a machine language code generated by a compiler and a high-level language code executable by a computer through an interpreter and the like.

Further, the method according to the disclosed embodiments of the present invention is included in a computer program product. The computer program product as a product may be traded between a seller and a buyer.

The computer program product may include an S/W program and a computer readable storage medium in which the S/W program is stored. For example, the computer program product may include an S/W program type product (e.g., downloadable app) electronically distributed through a manufacturing company of an electronic device or electronic market (e.g., Google play store, an app store, etc.). To do such electronic distribution, at least a portion of the S/W program may be stored in the storage medium or temporarily produced. In this case, the storage medium may be a storage medium of a server of the manufacturing company, a server of the electronic market, or a broadcast server for temporarily storing the S/W program.

The computer program product may include a storage medium of a server or a storage medium of a client device in a system composed of the server and the client device. If a third device (e.g., smartphone) connected to the server or client device exists, the computer program product may include a storage medium of the third device. Otherwise, the computer program product may include an S/W program itself transmitted from the server to the client device or the third device or from the third device to the client device.

In this case, one of the client device and the third device executes the computer program product to perform the method according to the embodiments of the present invention. Further, two or more devices of the server, the client device and the third device execute the computer program product to distributedly perform the method according to the embodiments of the present invention.

For example, the server (e.g., a cloud server or artificial intelligence server) executes the computer program product stored therein and controls the client device connected thereto to perform the method according to the embodiments of the present invention.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

The invention claimed is:

1. A method for providing information needed for diagnosis of lymph node metastasis of a thyroid cancer, the method comprising:
    acquiring medical images produced correspondingly to continuous volumes of a body region including a neck;
    detecting at least one or more lymph nodes from the medical images through a first network function learned, the lymph nodes including at least one or more lymph nodes having higher lymph node metastasis risks than a given reference value;
    dividing a neck tissue around a thyroid into a plurality of compartments on the medical images through a second network function learned, based on anatomical characteristics of the neck tissue;
    calculating cancer metastasis seriousness, based on at least one of a number of lymph nodes included in respective compartments, volumes of the lymph nodes, and cancer metastasis risks of the lymph nodes; and
    matching diagnostic information including information of the detected lymph nodes and the plurality of compartments with the medical images and displaying the diagnostic information on the medical images,
    wherein the diagnostic information comprises at least one of identifiers of the lymph nodes, position coordinates of the lymph nodes, the volumes of the lymph nodes, compartments where the lymph nodes are included, the cancer metastasis risks of the lymph nodes, and the cancer metastasis seriousness for the respective compartments.

2. The method according to claim 1, further comprising setting an excising region among the plurality of compartments, based on the calculated cancer metastasis seriousness.

3. The method according to claim 1, further comprising calculating the respective volumes of the lymph nodes and the compartments where the lymph nodes are included among the plurality of compartments.

4. The method according to claim 1, further comprising detecting the thyroid from the medical images through a third network function learned, the diagnostic information further including information of the detected thyroid.

5. The method according to claim 1, further comprising estimating a cancer metastasis process from the detected lymph nodes.

6. An apparatus for providing information needed for diagnosis of lymph node metastasis of a thyroid cancer, the apparatus comprising:
    a processor; and
    a memory for storing a program executable by the processor,
    wherein the processor executes the program to acquire medical images produced correspondingly to continuous volumes of a body region including a neck, detect at least one or more lymph nodes from the medical images through a first network function learned, divide a neck tissue around a thyroid into a plurality of compartments on the medical images through a second network function learned, based on anatomical characteristics of the neck tissue, calculate cancer metastasis seriousness, based on at least one of a number of lymph nodes included in respective compartments, volumes of the lymph nodes, and cancer metastasis risks of the lymph nodes, match diagnostic information including information of the detected lymph nodes and the plurality of compartments with the medical images, and display the diagnostic information on the medical images,
    wherein the lymph nodes comprise at least one or more lymph nodes having higher lymph node metastasis risks than a given reference value, and
    wherein the diagnostic information comprises at least one of identifiers of the lymph nodes, position coordinates of the lymph nodes, the volumes of the lymph nodes, compartments where the lymph nodes are included, the cancer metastasis risks of the lymph nodes, and the cancer metastasis seriousness for the respective compartments.

7. A computer program stored in a non-transitory recording medium to execute the method according to claim 1.

* * * * *